United States Patent [19]

Brown et al.

[11] Patent Number: 4,539,207

[45] Date of Patent: Sep. 3, 1985

[54] PYRIMIDINE COMPOUNDS

[75] Inventors: Thomas H. Brown, Welwyn Garden City; Robert J. Ife, Stevenage, both of England

[73] Assignee: Smith Kline & French Laboratories Limited, Welwyn Garden City, England

[21] Appl. No.: 156,523

[22] Filed: Jun. 4, 1980

Related U.S. Application Data

[62] Division of Ser. No. 9,990, Feb. 7, 1979, Pat. No. 4,234,588.

[51] Int. Cl.³ .................. C07D 401/12; A61K 31/505
[52] U.S. Cl. ..................................... 514/272; 544/320; 544/321; 544/322; 544/239; 544/405
[58] Field of Search ...................... 544/320, 322, 321; 424/251

[56] References Cited

U.S. PATENT DOCUMENTS

| 3,932,644 | 1/1976 | Durant et al. | 424/263 |
|---|---|---|---|
| 4,128,658 | 12/1978 | Orice et al. | 424/205 |
| 4,145,546 | 3/1979 | Brown et al. | 424/263 |
| 4,154,834 | 5/1979 | Brown et al. | 424/251 |
| 4,159,329 | 6/1979 | Brown et al. | 544/321 |
| 4,216,318 | 8/1980 | Brown et al. | 544/295 |

FOREIGN PATENT DOCUMENTS

| 849810 | 12/1975 | Belgium . |
|---|---|---|
| 857388 | 8/1976 | Belgium . |
| 867105 | 5/1977 | Belgium . |
| 877859 | 11/1979 | Belgium . |

*Primary Examiner*—Nicholas S. Rizzo
*Attorney, Agent, or Firm*—Joan S. Keps; Richard D. Foggio; Alan D. Lourie

[57] ABSTRACT

The compounds are substituted pyrimidine compounds which are histamine $H_2$-antagonists. A specific compound of the present invention is 2-[2-(5-dimethylaminomethyl)-2-furylmethylthio)ethylamino]-5-(3-pyridylmethyl)-4-pyrimidone.

25 Claims, No Drawings

PYRIMIDINE COMPOUNDS

This is a division of application Ser. No. 009,990 filed Feb. 7, 1979, now U.S. Pat. No. 4,234,588.

This invention relates to pyrimidine compounds, to pharmaceutical compositions containing them, to methods of blocking histamine H$_2$-receptors by administering them, and to a process for preparing some of these compounds.

Many physiologically-active substances elicit their biological actions by interaction with specific sites known as receptors. Histamine is such a substance and has multiple biological actions. Those biological actions of histamine which are inhibited by drugs commonly called "antihistamines" (histamine H$_1$-antagonists), of which mepyramine, diphenhydramine and chlorpheniramine are typical examples, are mediated through histamine H$_1$-receptors. However, others of the biological actions of histamine are not inhibited by "antihistamines" (histamine H$_1$-antagonists) and actions of this type which are inhibited by burimamide are mediated through receptors which are termed histamine H$_2$-receptors. In this specification by histamine H$_2$-receptors is meant receptors defined by Black et al. (Nature, 236, 385 (1972)) as those histamine receptors which are not blocked by mepyramine but are blocked by burimamide. Compounds which block histamine H$_2$-receptors are referred to as histamine H$_2$-antagonists.

Blockade of histamine H$_2$-receptors is of value in inhibiting the biological actions of histamine which are not inhibited by "antihistamines" (histamine H$_1$-antagonists). Histamine H$_2$-antagonists are active, for example, as inhibitors of gastric acid secretion, as anti-inflammatory agents and as agents which act on the cardiovascular system, for example as inhibitors of the effects of histamine on blood pressure.

In some physiological conditions the biological actions of histamine are mediated through both histamine H$_1$- and H$_2$-receptors and blockade of both types of receptors is useful. These conditions include inflammation mediated by histamine, for example skin inflammation, and those hypersensitivity responses due to the action of histamine at H$_1$- and H$_2$-receptors, for example allergies.

The pyrimidine compounds of the present invention are histamine H$_2$-antagonists and also have histamine H$_1$-antagonist activity.

The present invention provides pyrimidines of Structure 1:

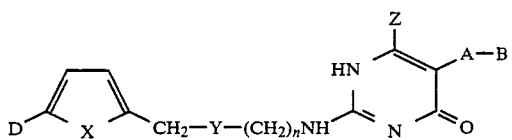

in which D is hydrogen or $R^1R^2N(CH_2)_m$—, $R^1$ and $R^2$ (which can be the same or different) are hydrogen, lower alkyl, aryl(lower alkyl), preferably phenyl(lower alkyl), or $R^1$ and $R^2$ taken together with the nitrogen atom shown can form a pyrrolidino or piperidino group, m is from 1 to 6, X is oxygen or sulphur, Y is sulphur, oxygen or methylene, n is 2 or 3, Z is hydrogen or lower alkyl, A is $C_1$–$C_5$ alkylene or —(CH$_2$)$_p$W(CH$_2$)$_q$— where W is oxygen or sulphur and p and q are such that their sum is from 1 to 4 and B is hydrogen, methyl, $C_3$–$C_6$ cycloalkyl, a heteroaryl group optionally substituted by one or more (which may be the same or different) of the groups lower alkyl, lower alkoxy, halo, hydroxy and amino, or B is a naphthyl, 6-(2,3-dihydro-1,4-benzodioxinyl), or a 4- or 5-(1,3-benzodioxolyl group, or a phenyl group optionally substituted with one or more (which may be the same or different) lower alkyl, lower alkoxy, halogen, aryl(lower alkoxy) (preferably phenyl(lower alkoxy), for example benzyloxy), hydroxy, loweralkoxy-lower alkoxy, trifluoromethyl di(lower alkyl)amino, phenoxy, halophenoxy, lower alkoxyphenoxy, phenyl, halophenyl or lower alkoxyphenyl groups.

The compounds of Structure 1 can be in the form of the free bases or their pharmaceutically acceptable acid addition salts.

Throughout this specification by the terms 'lower alkyl' and 'lower alkoxy' is meant alkyl and alkoxy groups which can be straight or branched and which contain 1 to 4 carbon atoms. Examples of heteroaryl groups are pyridyl, pyridyl N-oxide, furyl, thienyl, thiazolyl, oxazolyl, isothiazolyl, imidazolyl, pyrimidyl, pyrazinyl, pyridazyl, thiadiazolyl, quinolyl, isoquinolyl, 5,6,7-8-tetrahydroquinolyl, 1,3-dioxolopyridyl, benzimidazolyl and benzthiazolyl.

Preferably $R^1$ and $R^2$ are hydrogen, lower alkyl (especially methyl) or 2-phenylethyl or $R^1$ and $R^2$ taken together with the nitrogen atom shown can form a pyrrolidino or piperidino group. Particularly preferably $R^1$ and $R^2$ are both methyl.

Preferably m is from 1 to 3, especially 1.

Preferably X is oxygen.

Preferably Y is sulphur or methylene, especially sulphur.

Preferably n is 2.

Preferably Z is methyl. Especially Z is hydrogen. Other examples of Z are ethyl and n-propyl.

When B is an optionally substituted phenyl group it is preferably substituted by one or more lower alkoxy groups, and in particular is 3-methoxyphenyl, 4-methoxyphenyl or 3,4-dimethoxyphenyl.

A particularly valuable group of compounds is that in which B is a 6-(2,3-dihydro-1,4-benzodioxinyl), 5-(1,3-benzodioxolyl) or 1-naphthyl group.

Where B is a heteroaryl group it is preferably a 2-furyl, 2-thienyl, 2-pyridyl, 3-pyridyl, 4-pyridyl, 2-thiazolyl, 2-imidazolyl, 2-pyrimidyl, 2-pyrazyl, 3-pyridazyl, 3-quinolyl or 1-isoquinolyl group, which group is optionally substituted by one or more lower alkyl or lower alkoxy groups or a pyridyl or pyrimidyl group substituted by hydroxy, and especially 3-pyridyl, 6-methyl-3-pyridyl, 5,6-dimethyl-3-pyridyl, 6-methoxy-3-pyridyl, 2-methoxy-4-pyridyl, 6-hydroxy-3-pyridyl and 2-hydroxy-4-pyridyl.

Preferably in the compounds of Structure 1 either A is α,ω-straight or branched alkylene, preferably straight and especially methylene (—CH$_2$—), or A is —(CH$_2$)$_p$W(CH$_2$)$_q$— where p is 0, W is oxygen and q is 1 (i.e. A is a —OCH$_2$—, oxymethyl, group). Other examples of A are methoxymethyl, methylthiomethyl, methoxyethyl and methylthioethyl.

The compounds of Structure 1 are shown and described as 4-pyrimidone derivatives and these derivatives exist in equilibrium with the corresponding 6-one tautomers. These compounds also exist to a lesser extent as the hydroxy tautomers, and the pyrimidone ring may also exist in the following tautomeric forms:

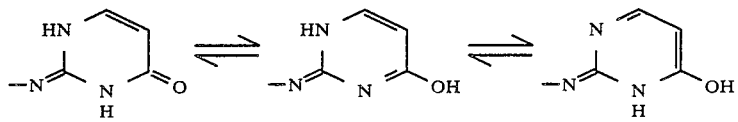

This invention includes the obvious chemical equivalents of the compounds of Structure 1, for example, those compounds with additional substituents on a furyl or thienyl group which do not substantially qualitatively affect the essential utility possessed by the compounds of Structure 1.

The compounds of Structure 1 can be prepared by reacting an amine of Structure 2

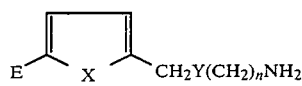

in which E is hydrogen or $R^3R^4N(CH_2)_m$—, where $R^3$ is $R^1$ and $R^4$ is $R^2$ or a monovalent amino-protecting group, provided that $R^3$ and $R^4$ are not both hydrogen and $R^3$ and $R^4$ together can form a divalent amino-protecting group, with a pyrimidone of Structure 3

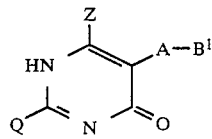

where $B^1$ has the same significance as B or is a protected derivative of B, Q is nitroamino ($NO_2NH$—), lower alkylthio, benzylthio, chlorine, bromine or other group which can be displaced with a primary amine, and subsequent removal of any protecting groups.

Preferably the monovalent amino-protecting group is t-butyloxycarbonyl (removed with trifluoroacetic acid) or benzyloxycarbonyl (removed with hydrogenolysis or with hydrogen bromide) and the divalent amino-protecting group is phthaloyl (removed with hydrazine).

By the term protected derivative of B is included precursors of B from which B can be generated directly, for example nitro-heteroaryl derivatives which can be reduced to give amino-heteroaryl derivatives. The compounds of Structure 1 in which B is a heteroaryl group substituted by hydroxy, particularly 6-hydroxy-3-pyridyl or 2-hydroxy-4-pyridyl, can be prepared by dealkylating the corresponding compounds of Structure 1 in which B is a heteroaryl group substituted by lower alkoxy or benzyloxy, and the alkyl and benzyl groups can be used as protecting groups. Preferably this dealkylation is carried out using ethanolic hydrochloric or hydrobromic acid at an elevated temperature, for example the boiling point of the mixture. Vicinal hydroxyl groups can be introduced as ketal derivatives.

Preferably Q is methylthio. Particularly preferably Q is nitroamino.

This process can be carried out in the absence of a solvent at an elevated temperature, e.g. when Q is methylthio at 150° C., or in the presence of a solvent, such as in refluxing pyridine. When Q is nitroamino this reaction is preferably carried out in a substantially inert solvent, for example refluxing ethanol.

The compounds of Structure 1 in which Y is sulphur can be prepared by (i) reacting a compound $GS(CH_2)_nNH_2$ where G is hydrogen or a thiol-protecting group, for example 4-methoxybenzyl, ethylcarbamoyl or —$S(CH_2)_nNH_2$ (in which the thiol is protected as the disulphide) and n is 2 or 3 with a pyrimidone of Structure 3, followed by removal of any thiol-protecting group present, and (ii) reacting the product with a compound of Structure 4

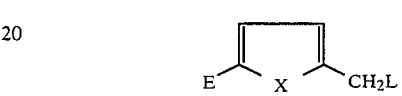

where E is as defined in Structure 2 and L is a group displaceable with a thiol, for example hydroxy, acyloxy (preferably acetoxy, methanesulphonyloxy or p-toluenesulphonyloxy), lower alkoxy (preferably methoxy), chlorine, bromine or triarylphosphonium (preferably triphenylphosphonium), and removal of any protecting groups.

Preferably step (i) is carried out under conditions described above for the reaction with the amine of Structure 2. Preferably in step (ii) L is hydroxy or methoxy and the reaction is carried out under acidic conditions, for example in aqueous hydrochloric or hydrobromic acid; when E is hydrogen and X is oxygen the compounds of Structure 4 are acid-labile and in step (ii) preferably L is chlorine or bromine and the reaction is carried out in the presence of a base, for example, with one equivalent of sodium ethoxide in ethanol.

The compounds of Structure 1 in which D is hydrogen can be converted into compounds of Structure 1 in which $R^1$ and $R^2$ are lower alkyl or $R^1R^2N$ forms a pyrrolidino or piperidino group and m is 1 provided that B is not a 5-unsubstituted furyl or thienyl group by reaction with a Mannich reagent, for example formaldehyde and an amine $R^1R^2NH$, or a di(lower alkyl)(methylene)ammonium salt (for example dimethyl(methylene)ammonium iodide). Preferably $R^1$ and $R^2$ are both methyl. Preferably when X is sulphur this reaction is carried out at about room temperature using dimethyl(methylene)ammonium chloride or iodide. When X is oxygen this reaction can be carried out using formalin (aqueous formaldehyde) in acetic acid or paraformaldehyde in ethanol, at an elevated temperature for example 100° C.

The compounds of Structure 1 in which $R^1$ or $R^2$ is hydrogen can be converted into the corresponding compound of Structure 1 in which $R^1$ or $R^2$ is methyl by reaction with formaldehyde and formic acid.

The amines of Structure 2 in which X is oxygen can be prepared by methods described in Belgian Pat. No. 857388, and the amines of Structure 2 in which X is sulphur can be prepared by analogous methods and by methods described in Belgian Pat. No. 867105, and variations thereof which are apparent to a skilled chemist. One particular method for the preparation of 5-(dialkylaminomethyl)-2-(hydroxymethyl)thiophenes is to react 2-hydroxymethylthiophene with a bis(dialkylamino)methane and formaldehyde in acetic acid.

The intermediates of Structure 3 in which Q is nitroamino can be prepared by reacting nitroguanidine with a compound of Structure 5

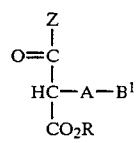

Structure 5 in which R is lower alkyl or aryl(lower alkyl), in the presence of a base. Preferably this reaction is carried out in a lower alkanol with a sodium lower alkoxide as the base at the boiling point of the reaction mixture.

The compounds of Structure 1 in which D is $R^1R^2N(CH_2)_m$— show both histamine $H_2$-antagonist and $H_1$-antagonist activity and have a particularly advantageous ratio of $H_2$ to $H_1$ activity. For example, the product of Example 1 (2-[2-(5-dimethylaminomethyl-2-furylmethylthio)ethylamino]-5-(3-pyridylmethyl)-4-pyrimidone) has a $pA_2$ value for the isolated guinea pig atrium test (histamine $H_2$-activity) which is greater than the $pA_2$ value for the guinea pig ileum test (histamine $H_1$-activity) by at least 2.0 (on a $\log_{10}$ scale).

The compounds of Structure 1 in which D is $R^1R^2N(CH_2)_m$— are well absorbed after oral administration and show good histamine $H_2$-antagonist activity when measured by inhibition of histamine-stimulated gastric secretion in the Heidenhain pouch dog after administration of the compounds by the oral route. For example in the latter test the product of Example 1 (2-[2-(5-dimethylaminomethyl-2-furylmethylthio)ethylamino]-5-(3-pyridylmethyl)-4-pyrimidone) is at least twice as active as the corresponding compound in which the 5-dimethylaminomethyl-2-furyl group is replaced by a 5-methyl-4-imidazolyl group.

The compounds of Structure 1 in which D is hydrogen are histamine $H_2$-antagonists and histamine $H_1$-antagonists and in the guinea pig ileum test for histamine $H_1$-antagonist activity have $pA_2$ values of greater than 5. These compounds differ from other compounds reported to be histamine $H_2$-antagonists in that in these compounds a basic heteroaryl group, a heteroaryl or aryl group with a basic substituent, or an isothioureido group is not an essential feature of their structure.

The activity of the compounds of Structure 1 as histamine $H_2$-antagonists can be demonstrated by the inhibition of histamine-stimulated secretion of gastric acid from the lumen-perfused stomachs of rats anaesthetised with urethane, at doses of less than 16 micromoles per kilogram intravenously. This procedure is referred to in Ash and Schild, Brit. J. Pharmac. Chemother. 27, 427 (1966). Their activity as histamine $H_2$-antagonists can also be demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus. They inhibit the basal secretion of gastric acid and also that stimulated by pentagastrin or by food. In a conventional test such as the measurement of blood pressure in the anaesthetised cat, at doses of from 0.5 to 256 micromoles per kilogram intravenously they inhibit the vasodilator action of histamine. The potency of these compounds is illustrated by the effective dose producing 50% inhibition of gastric acid secretion in the anaesthetised rat and the dose producing 50% inhibition of the histamine-induced tachycardia in the isolated guinea pig atrium (less than $10^{-4}$ Molar).

The activity of the compounds of Structure 1 as histamine $H_1$-antagonists can be demonstrated by the inhibition of histamine-stimulated contractions of the isolated guinea-pig ileum. A combination of histamine $H_1$- and $H_2$-antagonist activity is useful for treatment of inflammation in conditions where histamine is a mediator of inflammation, for instance in skin inflammation and those circumstances where there are hypersensitivity responses, for example allergies, due to the action of histamine at $H_1$- and $H_2$-receptors. It is advantageous to administer a single compound having histamine $H_1$- and $H_2$-antagonist activity rather than to administer individual compounds having histamine $H_1$-antagonist activity and histamine $H_2$-antagonist activity as difficulties arising from differing rates of absorption and pharmacokinetic characteristics are avoided.

The pharmaceutical compositions of the invention comprise a pharmaceutical carrier and a pharmacologically active compound of Structure 1 which can be in the base form or in the form of an addition salt with a pharmaceutically-acceptable acid. Such addition salts include those with hydrochloric, hydrobromic, hydriodic, sulphuric and maleic acids and may conveniently be formed from the corresponding compounds of Structure 1 by standard procedures, for example by treating them with an acid in a lower alkanol or by the use of ion exchange resins to form the required salt either directly from the compound in the base form from a different addition salt.

The pharmaceutical carrier employed can be a solid or liquid. Examples of solid carriers are lactose, maize starch, potato starch, or modified starches, dicalcium phosphate, terra alba, sucrose, celluloses, talc, gelatin, agar, pectin, acacia, magnesium stearate and stearic acid. Examples of liquid carriers are syrup, peanut oil, olive oil, alcohol, propylene glycol, polyethylene glycols and water.

If a solid carrier is used, the composition can be prepared in the form of a tablet, capsule containing powder or pellets, troche or lozenge. The amount of solid carrier in a unit dosage form is generally from about 25 mg to about 300 mg. If a liquid carrier is used, the composition can be in the form of a syrup, emulsion, multiple emulsion, sterile injectable liquid or an aqueous or non-aqueous solution or liquid suspension. Other additives such as preservatives, for example antioxidants or antibacterials, and/or flavouring or colouring agents can also be included. The sterile liquids can be prepared in ampoules, multidose vials or unit dose disposable systems. The preparation can also be in a semi-solid form, for example a cream, paste, ointment or gel, or in a liquid or aerosol form for topical application. The pharmaceutical compositions are prepared by conventional techniques involving procedures such as milling, mixing, granulating and compressing, spray drying, freeze drying or dissolving or dispersing the ingredients as appropriate to the desired preparation. The active ingredient is present in the compositions in an effective amount to block histamine $H_2$-receptors. Preferably, each dosage unit contains the active ingredient in an amount of from about 50 mg to about 250 mg.

A method of blocking histamine $H_2$-receptors by administering to an animal a compound of Structure 1 is also an object of this invention. Also, this invention includes a method of simultaneously blocking histamine $H_1$-receptors and histamine $H_2$-receptors by administering to an animal a compound of Structure 1 in which D is hydrogen.

The active ingredient is preferably administered one to six times per day. The daily dosage regimen is preferably from about 150 mg to about 1500 mg. The route of administration can be oral or parenteral.

This invention is illustrated but in no way limited by the following Examples, where all temperatures are in degrees Centigrade:

EXAMPLE 1

(a)(i) Sodium (1.15 g) was dissolved in methanol (50 ml), and nitroguanidine (4.7 g) was added to the cooled solution. The mixture was refluxed for 45 minutes, ethyl 2-formyl-3-(3-pyridyl)propionate (9.3 g) was added portionwise and the mixture was refluxed for 45 hours and evaporated to dryness. Water was added to the residue and the mixture was extracted with chloroform. The aqueous phase was adjusted to pH 5 with acetic acid, and the solid which was precipitated was filtered off, washed and dried to give 2-nitroamino-5-(3-pyridylmethyl)-4-pyrimidone, m.p. 214.5°–216°, in 38% yield.

(ii) A solution of 2-(5-dimethylaminomethyl-2-furylmethylthio)ethylamine (2.25 g, 0.105 mol) and 2-nitroamino-5-(3-pyridylmethyl)-4-pyrimidone (2.47 g, 0.100 mol) in ethanol (12 ml) was boiled under reflux for 22 hours and evaporated to dryness. The residue was washed with water to give 2-[2-(5-dimethylaminomethyl-2-furylmethylthio)ethylamino]-5-(3-pyridylmethyl)-4-pyrimidone and this was treated with dilute ethanolic hydrogen chloride and dried. The residue was recrystallised from methanol/2-propanol and from methanol to give 2-[2-(5-dimethylaminomethyl-2-furylmethylthio)ethylamino]-5-(3-pyridylmethyl)-4-pyrimidone trihydrochloride (2.61 g) m.p. 205°–208°.

(b)(i) 2-Nitroamino-5-(3-pyridylmethyl)-4-pyrimidone (12.36 g) was added to a stirred mixture of 2-(5-furylmethylthio)ethylamine hydrochloride (10.65 g) and sodium ethoxide (prepared from 1.26 g sodium) in dry ethanol (300 ml) and the mixture was boiled under reflux for 44 hours and evaporated to dryness. The residue was triturated with water (discarded) and recrystallised from aqueous 2-propanol to give 2-[2-(2-furylmethylthio)ethylamino]-5-(3-pyridylmethyl)-4-pyrimidone, m.p. 136°–139°.

(ii) A mixture of this pyrimidone (1.71 g), dimethylamine hydrochloric (0.51 g), aqueous formaldehyde (37% w/v, 0.5 ml) and acetic acid (10 ml) was heated at 100° for 20 minutes, allowed to stand at room temperature overnight and evaporated to dryness. The residue was dissolved in water and the mixture was basified with aqueous sodium carbonate. 2-[2-(5-Dimethylaminomethyl-2-furylmethylthio)ethylamino]-5-(3-pyridylmethyl)-4-pyrimidone precipitated out and was filtered off, combined with a residue obtained by evaporating an ethyl acetate extract of the aqueous phase, treated with ethanolic HCl and crystallised from methanol to give 2-[2-(5-dimethylaminomethyl-2-furylmethylthio)ethylamino]-5-(3-pyridylmethyl)-4-pyrimidone trihydrochloride m.p. 218°–220° C. (decomp)-mixed melting point with the product from (a)(ii) above was undepressed.

EXAMPLE 2

(i) A solution of ethyl 2-formyl-3-(5-(1,3-benzodioxolyl))propionate (7.5 g) in methanol (20 ml) was added to sodium methoxide in methanol (prepared from 0.689 g sodium and 50 ml methanol). Nitroguanidine (3.12 g) was added to this stirred mixture. The mixture was refluxed for 18 hours and evaporated to a residue. This residue was dissolved in water (200 ml) and the solution extracted with chloroform. The aqueous phase was adjusted to pH 5 with acetic acid and the white solid which precipitated out was filtered off to give 2-nitroamino-5-(5-(1,3-benzodioxolyl)methyl)-4-pyrimidone (4.08 g) m.p. 200°–202°. A sample recrystallised from aqueous acetic acid had m.p. 201.5°–202.5°.

(ii) A mixture of 2-(5-dimethylaminomethyl-2-furylmethylthio)ethylamine (3.50 g, 0.016 mol), 2-nitroamino-5-[5-(1,3-benzodioxolyl)methyl]-4-pyrimidone (4.64 g, 0.016 mol) and dry ethanol (25 ml) was boiled under reflux for 24 hours and evaporated to dryness. The residue was treated with an excess of aqueous hydrochloric acid (2N) and the mixture was filtered. The filtrate was treated with sodium hydrogen carbonate solution which caused 2-[2-(dimethylaminomethyl-2-furylmethylthio)ethylamino]-5-[5-(1,3-benzodioxolyl)ethyl]-4-pyrimidone to separate out as a gum. This gum was washed with water and was treated with an excess of ethanolic hydrogen chloride and evaporated to dryness. The residue was recrystallised three times from ethanol to give 2-[2-(5-dimethylaminomethyl-2-furylmethylthio)ethylamino]-5-[5-(1,3-benzodioxolyl)methyl]-4-pyrimidone dihydrochloride (0.85 g) m.p. 147°–148°.

EXAMPLE 3

(i) A mixture of 6-methylpyridine-3-carboxaldehyde (51.57 g), malonic acid (44.30 g), piperidine (6 ml) and pyridine (300 ml) was stirred at 100° for 3 hours and was allowed to cool. The mixture was evaporated to dryness, water was added to the residue and the solid was filtered off and recrystallised from ethanol-acetic acid to give 3-(6-methyl-3-pyridyl)acrylic acid (41.25 g) m.p. 213.5°–215.5°.

(ii) A stirred mixture of 3-(6-methyl-3-pyridyl)acrylic acid (50.70 g) dry ethanol (350 ml) and concentrated sulphuric acid (25 ml) was heated under reflux for 18 hours and ethanol (~250 ml) was removed by evaporation. The residue was poured into ice-aqueous ammonia and the mixture was extracted with ether. The ether extracts were washed with water and evaporated to an oil which crystallised on standing to give ethyl 3-(6-methyl-3-pyridyl)acrylate m.p. 36°–37°.

(iii) Ethyl 3-(6-methyl-3-pyridyl)acrylate (60.36 g) was hydrogenated in ethanol at 35° and 355 kPa using palladium-on charcoal catalyst (10%, 1.0 g). The mixture was filtered and the filtrate was evaporated to give ethyl 3-(6-methyl-3-pyridyl)propionate as an oil.

(iv) Ethyl 3-(6-methyl-3-pyridyl)propionate (57.79 g) and ethyl formate (23.71 g) were added over 2.5 hours to a stirred mixture of sodium wire (6.88 g) and ether (200 ml) cooled in an ice-salt bath. The mixture was stirred for 20 hours and the ether was removed by evaporation. Thiourea (22.76 g) and ethanol (175 ml) were added to the residue and the mixture was heated under reflux for 7 hours and evaporated to dryness. Water (200 ml) was added to the residue and the mixture was adjusted to pH 6 with acetic acid. The solid was filtered off and recrystallised from methanol/acetic acid to give 5-(6-methyl-3-pyridylmethyl)-2-thiouracil (17.24 g) m.p. 240°–241°.

(v) Methyl iodide (13.79 g) was added to a stirred solution of 5-(6-methyl-3-pyridylmethyl)-2-thiouracil (22.66 g) and sodium hydroxide (8.0 g) in water (250 ml), and the mixture was heated at 70° for 1 hour and stirred at room temperature overnight. Acetic acid was added until pH 5 and the volume of the mixture was evaporated to a volume of 50 ml. The solid was filtered off and was recrystallised from ethanol-acetic acid to give 5-(6-methyl-3-pyridylmethyl)-2-methylthio-4-pyrimidone (10.16 g) m.p. 197°–197.5°.

(vi) A mixture of 2-(5-dimethylaminomethyl-2-furylmethylthio)ethylamine (1.30 g), 5-(6-methyl-3-pyridylmethyl)-2-methylthio-4-pyrimidone (1.41 g) and pyridine (10 ml) was heated under reflux for 46 hours and evaporated to dryness. The residue was washed with hot water to give 2-[2-(5-dimethylaminomethyl-2-furylmethylthio)ethylamino]-5-(6-methyl-3-pyridylmethyl)-4-pyrimidone as an oil and this oil was treated with excess of hydrogen chloride in ethanol and evaporated to dryness. The residue was recrystallised from aqueous ethanol containing HCl to give 2-[2-(5-dimethylaminomethyl-2-furylmethylthio)ethylamino]-5-(6-methyl-3-pyridylmethyl)-4-pyrimidone trihydrochloride m.p. 210°–213°. A sample recrystallised a further time from aqueous ethanol containing HCl had m.p. 224°–227°.

EXAMPLE 4 a(i) n-Butyllithium in hexane (1.58 Molar, 50 ml) was added to a mixture of 2-(dimethylaminomethyl)thiophene (10 g) and dry tetrahydrofuran (50 ml) stirred under nitrogen and maintained at below 10° with an ice-salt bath. The mixture was allowed to warm to room temperature and was stirred for a further 2 hours. Paraformaldehyde (4.2 g) was added portionwise over 0.5 hour during which time the temperature was maintained below 30°. The mixture was stirred at room temperature for a further 0.5 hour and the gel was poured into water. The aqueous mixture was extracted with ether and the extracts were evaporated to dryness. Hydrogen chloride in ethanol and dry ether was added to the residue, and the solid was filtered off to give 2-(dimethylaminomethyl)-5-(hydroxymethyl)thiophene hydrochloride (9.33 g). A sample recrystallised from ethanol acetate/2-propanol had m.p. 134°–137°.

(ii) A solution of 2-(dimethylaminomethyl)-5-(hydroxymethyl)thiophene hydrochloride (8.0 g) in concentrated hydrochloric acid (50 ml) was added dropwise to a stirred solution of cysteamine hydrochloride (4.37 g) in concentrated hydrochloric acid (50 ml) cooled in an ice-bath. The temperature of the mixture was maintained below 5° during the addition. The mixture was allowed to reach room temperature and was stirred overnight and poured into water. The aqueous mixture was adjusted to pH12 with 2N sodium hydroxide and was extracted with ethyl acetate (750 ml). The extract was dried and evaporated to give an oil which was dissolved in dry ether and hydrogen chloride in ethanol was added and the solid was filtered off to give 2-[5-dimethylaminomethyl-2-thienylmethylthio]ethylamine dihydrochloride (8.44 g) m.p. 190°–194°.

(iii) 2-[5-Dimethylaminomethyl-2-thienylmethylthio]ethylamine dihydrochloride (2.0 g) was added to a solution of sodium ethoxide (prepared from 0.304 g sodium) in ethanol (60 ml) and the mixture was boiled under reflux for 2 hours. The cooled mixture was filtered and 2-nitroamino-5-(3-pyridylmethyl)-4-pyrimidone (1.63 g) was added to the filtrate and was boiled under reflux for 40 hours and evaporated to dryness. The residue was triturated with water and was crystallised from ethyl acetate to give 2-[2-(5-dimethylaminomethyl-2-thienylmethylthio)ethylamino]-5-(3-pyridylmethyl)-4-pyrimidone which was hygroscopic and was treated with aqueous hydrobromic acid and crystallised from methanol as the trihydrobromide, m.p. 233°–237°.

(b)(i) Cysteamine hydrochloride (9.95 g) was dissolved in concentrated hydrochloric acid (50 ml) and the solution was cooled to 0°. 2-Hydroxymethylthiophene (10 g) was added dropwise to the stirred solution which was maintained at below 5°. The mixture was stirred overnight at room temperature, adjusted to pH 10 with concentrated aqueous sodium hydroxide and extracted with ethyl acetate. The extracts were evaporated and the residue was distilled at 158°–164°/760 mm Hg to give 2-(2-thienylmethylthio)ethylamine which was converted into the hydrochloride, m.p. 108°–111°, by treatment with ethanolic HCl and ether.

(ii) 2-(2-Thienylmethylthio)ethylamine hydrochloride (2 g) in ethanol (25 ml) was added to a solution of sodium ethoxide (prepared from 0.218 g sodium) in ethanol and the mixture was stirred for 0.5 hour. 2-Nitroamino-5-(3-pyridylmethyl)-4-pyrimidone (2.34 g) was added and the mixture was boiled under reflux for 40 hours and evaporated to dryness. Pyridine (50 ml) was added to the residue and the mixture was boiled under reflux for 24 hours and evaporated. The residue was crystallised from ethanol/ethyl acetate and further purified by elution from a column of silica gel with ethyl acetate/methanol (5.1) and recrystallisation from 2-propanol to give 2-[2-(2-thienylmethylthio)ethylamino]-5-(3-pyridylmethyl)-4-pyrimidone m.p. 145°–148°.

(iii) 2-[2-(2-Thienylmethylthio)ethylamino]-5-(3-pyridylmethyl)-4-pyrimidone is reacted with an excess of dimethyl(methylene)ammonium iodide in dimethylformamide at room temperature to give 2-[2-(5-dimethylaminomethyl-2-thienylmethylthio)ethylamino]-5-(3-pyridylmethyl)-4-pyrimidone.

EXAMPLE 5

(i) 3-Chloroperoxybenzoic acid (10.35 g) was added to 2-nitroamino-5-(3-pyridylmethyl)-4-pyrimidone (12.35 g) (from Example 1(a)(i)) in acetic acid (300 ml) and the mixture was stirred at room temperature for 18 hours and at 60° for 5 hours and allowed to cool to room temperature. The solid was filtered off and purified by precipitation from solution in dilute sodium hydroxide by the addition of hydrochloric acid to give 2-nitroamino-5-(3-pyridylmethyl)-4-pyrimidone pyrid-N-oxide m.p. 271° (decomp).

(ii) A mixture of the N-oxide (1.84 g) and 2-(5-dimethylaminomethyl)-2-furylmethylthio)ethylamine (2.14 g) was warmed on water-bath, ethanol (25 ml) was added and the mixture was boiled under reflux for 30 hours and evaporated to dryness. The residue was washed with water and the oil crystallised from 2-propanol to give 2-[2-(5-dimethylaminomethyl-2-furylmethylthio)ethylamino]-5-(3-pyridylmethyl)-4-pyrimidone pyrid-N-oxide m.p. 50°–55°.

EXAMPLE 6

(i) A mixture of ethyl formate (111 g) and 2-butanone (108 g) was added dropwise to a stirred mixture of sodium hydride in oil (50% w/w, 72 g) in dry dimethoxyethane and the mixture was allowed to stand overnight. Ether (800 ml) was added and the solid (101 g) was filtered off. Cyanoacetamide (69.5 g), piperidine acetate (prepared by adding piperidine to acetic acid (7 ml) and water (18 ml) until the mixture was basic) and water (400 ml) were added to this solid and the mixture was heated under reflux for 2 hours and allowed to cool. The mixture was acidified with acetic acid and the solid which precipitated out was recrystallised from aqueous ethanol to give 3-cyano-5,6-dimethyl-2-hydroxypyridine (43.5 g).

(ii) An intimate mixture of 3-cyano-5,6-dimethyl-2-hydroxypyridine (42 g) and phosphorus pentachloride (81 g) was heated at 140°–160° for 2 hours. Phosphoryl chloride was removed by distillation under reduced pressure and ice-water (500 g) was added to the residue. The mixture was adjusted to pH 7 with aqueous sodium hydroxide and extracted with ether. The ether extracts were evaporated to an oil which was crystallised from ether/petroleum ether (b.p. 60°–80°) to give 2-chloro-3-cyano-5,6-dimethylpyridine (25.3 g) m.p. 83°–87°.

(iii) A mixture of 2-chloro-3-cyano-5,6-dimethylpyridine (21.5 g) semicarbazide hydrochloride (24.0 g), sodium acetate (42.3 g), water (225 ml) and methanol (475 ml) was hydrogenated at 344 kPa at 50° using Raney nickel catalyst (5 g). The mixture was added to water (750 ml) and filtered. The solid filtered off was suspended in water (130 ml) and concentrated hydrochloric acid (70 ml) was added and the mixture was heated at 100° for 1 hour, formalin (40% w/w, 120 ml) was added and the mixture was heated at 100° for a further 0.5 hour and allowed to cool. Sodium acetate (95 g) and water (250 ml) were added and the mixture was extracted with ether and the extracts were washed with 5% aqueous potassium carbonate and evaporated to give 2-chloro-5,6-dimethyl-3-pyridinecarboxaldehyde (13.24 g, 60%) m.p. 69°–70°.

(iv) A mixture of 2-chloro-5,6-dimethyl-3-pyridinecarboxaldehyde (16.85 g), malonic acid (11.45 g) piperidine (10 ml) and pyridine (100 ml) was heated under reflux for 1 hour and evaporated to an oil. This oil was dissolved in sodium hydroxide solution and was extracted with chloroform (discarded). The aqueous phase was acidified with hydrochloric acid and was extracted with chloroform. The chloroform extracts were washed with water and evaporated to give 3-(2-chloro-5,6-dimethyl-3-pyridyl)acrylic acid (18.3 g, 87%) m.p. 150°–158°. This acid was esterified using ethanol and sulphuric acid to give the ethyl ester m.p. 85°–88°.

(v) Ethyl 3-(2-chloro-5,6-dimethyl-3-pyridyl)acrylate (32.7 g) in ethanol (500 ml) was hydrogenated at 25°–30° and 344 kPa using palladium-on-charcoal catalyst (5%, 3 g). The mixture was filtered and the filtrate was evaporated to an oil which was partitioned between chloroform and 2N hydrochloric acid. The aqueous phase was made basic with aqueous sodium hydroxide, extracted with chloroform and the chloroform extracts were evaporated to give ethyl 3-(5,6-dimethyl-3-pyridyl)propionate (21.8 g, 80%) as an oil.

(vi) Reaction of ethyl 3-(5,6-dimethyl-3-pyridyl)propionate with ethyl formate and sodium hydride in dimethoxyethane at room temperature gave 3-(5,6-dimethyl-3-pyridyl)-2-formylpropionate m.p. 148°–149°.

(vii) Nitroguanidine (6.05 g) was added to a solution of sodium methoxide (prepared from 1.45 g sodium) in dry methanol (65 ml) and the mixture was boiled under reflux for 0.75 hours. 3-(5,6-Dimethyl-3-pyridyl)-2-formylpropionate (14.3 g) was added and the mixture was boiled under reflux for 40 hours and evaporated to dryness. Water (40 ml) was added to the residue and the mixture was extracted with chloroform (discarded). The aqueous phase was adjusted to pH 6 with hydrochloric acid and the solid which separated out was filtered off and recrystallised from dimethylformamide-ethanol to give 5-(5,6-dimethyl-3-pyridylmethyl)-2-nitroamino-4-pyrimidone m.p. 212°–213°.

(viii) A mixture of 2-(5-dimethylaminomethyl)-2-furylmethylthio)ethylamine (1.39 g), (5-(5,6-dimethyl-3-pyridylmethyl)-2-nitroamino-4-pyrimidone (1.51 g) and ethanol (25 ml) was boiled under reflux for 48 hours and evaporated to dryness. The residue was triturated with water (discarded) to leave 2-[2-(5-dimethylaminomethyl-2-furylmethylthio)ethylamino]-5-(5,6-dimethyl-3-pyridylmethyl)-pyrimidone which was treated with ethanolic HCl and recrystallised three times from methanol/ethanol to give 2-[2-(5-dimethylaminomethyl-2-furylmethylthio)ethylamino]-5-(5,6-dimethyl-3-pyridylmethyl)-4-pyrimidone trihydrochloride m.p. 221°–224°.

EXAMPLE 7

(i) 2-Chloro-4-cyanopyridine (115.53 g) in methanol/dioxan (1:1, 850 ml) was added to a solution of sodium methoxide (prepared from 20.8 g sodium) in methanol (285 ml) and the mixture was boiled under reflux for 2.5 hours and was allowed to cool. The mixture was filtered and the volume of the filtrate was reduced by evaporation to 200 ml and water (400 ml) was added. The solid which precipitated out was filtered off to give 2-methoxy-4-cyanopyridine (57.2 g, 51%) m.p. 93°–95.5°.

(ii) A mixture of 2-methoxy-4-cyanopyridine (57.2 g), semicarbazide hydrochloride (71.24 g), sodium acetate (69.86 g), ethanol (1200 ml) and water (370 ml) was hydrogenated at 344 kPa using Raney nickel catalyst (1.0 g). The mixture was evaporated to a volume of 450 ml, water (900 ml) was added and the mixture was allowed to stand at 0° overnight. The mixture was filtered and the solid was washed with water and was dissolved in 10% hydrochloric acid (950 ml). Formaldehyde solution (36% w/v, 420 ml) was added and the mixture was warmed for 30 minutes, allowed to cool and was added to a solution of sodium acetate (280 g) in water (840 ml). The mixture was extracted with ether (3×500 ml) and the combined extracts were successively washed with aqueous potassium carbonate and water and were dried and evaporated to give 2-methoxypyridine-4-carboxaldehyde (20.53 g, 35%) m.p. 33°–35°. A sample recrystallised from petroleum ether had m.p. 33°–36°.

(iii) Condensation of 2-methoxypyridine-4-carboxaldehyde with malonic acid with subsequent esterification and hydrogenation according to the procedure of Example 3(i)-(iii) and formylation of the product with ethyl formate and sodium hydride gave ethyl 2-formyl-3-(2-methoxy-4-pyridyl)-propionate as an oil, and treatment of this with nitroguanidine and sodium methoxide according to the procedure of Example 6(vii) gave 2-nitroamino-5-(2-methoxy-4-pyridylmethyl)-4-pyrimidone in 59% yield, m.p. 194°–195.5° (from aqueous acetic acid).

(iv) A mixture of 2-(5-dimethylaminomethyl-2-furylmethylthio)ethylamine (2.50 g), 2-nitroamino-5-(2-methoxy-4-pyridylmethyl)-4-pyrimidone (2.77 g) and ethanol (15 ml) was boiled under reflux for 19 hours and evaporated. The residue was triturated with hot water to leave 2-[2-(5-dimethylaminomethyl-2-furylmethylthio)ethylamino]-5-(2-methoxy-4-pyridylmethyl)-4-pyrimidone. A mixture of this pyrimidone (3.04 g), 2N hydrogen chloride in ethanol (20 ml) and ethanol (80 ml) was boiled under reflux for 48 hours and evaporated to dryness. The residue was recrystallised from methanol/ethanol to give 2-[2-(5-dimethylaminomethyl-2-furylmethylthio)ethylamino]-5-(2-hydroxy-4-pyridylmethyl)-4-pyrimidone trihydrochloride m.p. 181°–185°.

EXAMPLE 8

Reaction of 5-(3-methoxybenzyl)-2-methylthio-4-pyrimidone with one equivalent of
(a) 2-[5-methylaminomethyl-2-furylmethylthio]-ethylamine
(b) 2-[5-dimethylaminomethyl-2-furylmethylthio]ethylamine
(c) 2-[5-(4-(dimethylamino)butyl)-2-furylmethylthio]-ethylamine
(d) 4-[5-dimethylaminomethyl-2-furyl]butylamine by heating at 140°–150° for 1 hour, and purification by recrystallisation of the residue gives
(a) 2-[2-(5-methylaminomethyl-2-furylmethylthio)-ethylamino]-5-(3-methoxybenzyl)-4-pyrimidone
(b) 2-[2-(5-dimethylaminomethyl-2-furylmethylthio)-ethylamino]-5-(3-methoxybenzyl)-4-pyrimidone
(c) 2-[5-(4-(dimethylamino)butyl)-2-furylmethylthio)-ethylamino]-5-(3-methoxybenzyl)-4-pyrimidone
(d) 2-[4-(5-dimethylaminomethyl-2-furyl)butylamino]-5-(3-methoxybenzyl)-4-pyrimidone

EXAMPLE 9

Reaction of
(a) 5-(3-pyridylmethyl)-2-methylthio-4-pyrimidone
(b) 5-[5-(1,3-benzodioxolyl)methyl]-2-methylthio-4-pyrimidone
with one equivalent of
(i) 2-[5-methylaminomethyl-2-furylmethylthio]-ethylamine
(ii) 2-[5-(4-(dimethylamino)butyl)-2-furylmethylthio]-ethylamine
(iii) 4-[5-dimethylaminomethyl-2-furyl]butylamine by heating at 140°–150° for 1 hour, and purification of the residue gives:
(a)(i) 2-[2-(5-methylaminomethyl-2-furylmethylthio)ethylamino]-5-(3-pyridylmethyl-4-pyrimidone
(ii) 2-[2-(5-(4-(dimethylamino)butyl)-2-furylmethylthio)ethylamino]-5-(3-pyridylmethyl)-4-pyrimidone
(iii) 2-[4-(5-dimethylaminomethyl-2-furyl)butylamino]-5-(3-pyridylmethyl)-4-pyrimidone
and
(b)(i) 2-[2-(5-methylaminomethyl-2-furylmethylthio)-ethylamino]-5-(5-(1,3-benzodioxolyl)methyl)-4-pyrimidone
(ii) 2-[5-(4-(dimethylamino)butyl)-2-furylmethylthio)-ethylamino]-5-(5-(1,3-benzodioxolyl)methyl)-4-pyrimidone
(iii) 2-[4-5-dimethylaminomethyl-2-furyl)butylamino)-5-(5-(1,3-benzodioxolyl)methyl)-4-pyrimidone

EXAMPLE 10

Reaction of
(a) 5-(1-naphthylmethyl)-2-methylthio-4-pyrimidone
(b) 5-(3-quinolylmethyl)-2-methylthio-4-pyrimidone with one equivalent of 2-[5-dimethylaminomethyl-2-furylmethylthio]ethylamine by refluxing pyridine for 24 hours gives (a) 2-[2-(5-dimethylaminomethyl-2-furylmethylthio)ethylamino]-5-(1-naphthylmethyl)-4-pyrimidone
(b) 2-[2-(5-dimethylaminomethyl-2-furylmethylthio)ethylamino]-5-(3-quinolylmethyl)-4-pyrimidone

EXAMPLE 11

Reaction of
(a) 5-(2-pyridylmethyl)-2-methylthio-4-pyrimidone
(b) 5-(4-pyridylmethyl)-2-methylthio-4-pyrimidone
(c) 5-(2-thienylmethyl)-2-methylthio-4-pyrimidone
(d) 5-(4-methylbenzyl)-2-methylthio-4-pyrimidone
(e) 5-(3,4,5-trimethoxybenzyl)-2-methylthio-4-pyrimidone
(f) 5-(4-chlorobenzyl)-2-methylthio-4-pyrimidone
(g) 5-(2-chlorobenzyl)-2-methylthio-4-pyrimidone
(h) -5-(3,4-dichlorobenzyl)-2-methylthio-4-pyrimidone
with one equivalent of 2-[5-dimethylaminomethyl-2-furylmethylthio]ethylamine by boiling under reflux in pyridine for 24 hours gives
(a) 2-[2-(5-dimethylaminomethyl-2-furylmethylthio)ethylamino]-5-(2-pyridylmethyl)-4-pyrimidone
(b) 2-[2-(5-dimethylaminomethyl-2-furylmethylthio)ethylamino]-5-(4-pyridylmethyl)-4-pyrimidone
(c) 2-[2-(5-dimethylaminomethyl-2-furylmethylthio)ethylamino]-5-(2-thienylmethyl)-4-pyrimidone
(d) 2-[2-(5-dimethylaminomethyl-2-furylmethylthio)ethylamino]-5-(4-methylbenzyl)-4-pyrimidone
(e) 2-[2-(5-dimethylaminomethyl-2-furylmethylthio)ethylamino]-5-(3,4,5-trimethoxybenzyl)-4-pyrimidone
(f) 2-[2-(5-dimethylaminomethyl-2-furylmethylthio)ethylamino]-5-(4-chlorobenzyl)-4-pyrimidone
(g) 2-[2-(5-dimethylaminomethyl-2-furylmethylthio)ethylamino]-5-(2-chlorobenzyl)-4-pyrimidone
(h) 2-[2-(5-dimethylaminomethyl-2-furylmethylthio)ethylamino]-5-(3,4-dichlorobenzyl)-4-pyrimidone

EXAMPLE 12

Reaction of
(a) 5-benzyloxy-2-methylthio-4-pyrimidone
(b) 5-(2-(4-methoxybenzyloxy)ethyl)-2-methylthio-4-pyrimidone
(c) 5-(2-(4-methoxybenzylthio)ethyl)-2-methylthio-4-pyrimidone
(d) 5-(2-(3-pyridylmethylthio)ethyl)-2-methylthio-4-pyrimidone
(e) 5-(2-phenylethyl)-2-methylthio-4-pyrimidone
(f) 5-(2-phenylethyl)-6-methyl-2-methylthio-4-pvrimidone
(g) 5-(4-phenylbutyl)-2-methylthio-4-pyrimidone with one equivalent of 2-[5-dimethylaminomethyl-2-furylmethylthio]ethylamine by boiling under reflux in pyridine for 24 hours gives
(a) 2-[2-(5-dimethylaminomethyl-2-furylmethylthio)ethylamino]-5-benzyloxy-4-pyrimidone
(b) 2-[2-(5-dimethylaminomethyl-2-furylmethylthio)ethylamino]-5-(2-(4-methoxybenzyloxy)ethyl)-4-pyrimidone
(c) 2-[2-(5-dimethylaminomethyl-2-furylmethylthio)ethylamino]-5-(2-(4-methoxybenzylthio)ethyl-4-pyrimidone
(d) 2-[2-(5-dimethylaminomethyl-2-furylmethylthio)ethylamino]-5-(2-(3-pyridylmethylthio)ethyl)-4-pyrimidone
(e) 2-[2-(5-dimethylaminomethyl-2-furylmethylthio)ethylamino]-5-(2-phenylethyl)-4-pyrimidone
(f) 2-[2-(5-dimethylaminomethyl-2-furylmethylthio)ethylamino]-5-(2-phenylethyl)-6-methyl-4-pyrimidone (g) 2-[2-(5-dimethylaminomethyl-2-furylmethylthio)ethylamino]-5-(4-phenylbutyl)-4-pyrimidone

EXAMPLE 13

Substitution of
(a) 2-(5-(2-phenylethylaminomethyl)-2-furylmethylthio)ethylamine
(b) 2-(5-(1-piperidinyl)methyl-2-furylmethylthio)ethylamine
(c) 2-(5-(1-pyrrolidino)methyl-2-furylmethylthio)ethylamine
(d) 5-(5-dimethylaminomethyl-2-furyl)pentylamine
(e) 3-(5-dimethylaminomethyl-2-furylmethylthio)propylamine
(f) 2-(5-dimethylaminomethyl-2-furylmethoxy)ethylamine for 2-(5-dimethylaminomethyl-2-furylmethylthio)ethylamine in the procedure of Example 1(ii) gives:
(a) 2-[2-(5-(2-phenylethylaminomethyl)-2-furylmethylthio)ethylamino]-5-(3-pyridylmethyl)-4-pyrimidone
(b) 2-[2-(5-(1-piperidinyl)methyl-2-furylmethylthio)ethylamino]-5-(3-pyridylmethyl)-4-pyrimidone
(c) 2-[2-(5-(1-pyrrolidino)methyl-2-furylmethylthio)ethylamino]-5-(3-pyridylmethyl)-4-pyrimidone
(d) 2-[5-(5-dimethylaminomethyl-2-furyl)pentylamino]-5-(3-pyridylmethyl)-4-pyrimidone
(e) 2-[3-(5-dimethylaminomethyl-2-furylmethylthio)propylamino]-5-(3-pyridylmethyl)-4-pyrimidone
(f) 2-[2-(5-dimethylaminomethyl-2-furylmethoxy)ethylamino]-5-(3-pyridylmethyl)-4-pyrimidone

EXAMPLE 14

Substitution of
(a) 4-(5-dimethylaminomethyl-2-thienyl)butylamine
(b) 2-(5-dimethylaminomethyl-2-thienylmethoxy)ethylamine
(c) 2-(5-methylaminomethyl-2-thienylmethylthio)ethylamine
(d) 2-(5-(1-pyrrolidino)methyl-2-thienylmethylthio)ethylamine
(e) 2-(5-methylethylaminomethyl-2-thienylmethylthio)ethylamine
for 2-(5-dimethylaminomethyl-2-furylmethylthio)ethylamine in the procedure of Example 1(ii) gives:
(a) 2-[4-(5-dimethylaminomethyl-2-thienyl)butylamino]-5-(3-pyridylmethyl)-4-pyrimidone
(b) 2-[2-(5-dimethylaminomethyl-2-thienylmethoxy)ethylamino]-5-(3-pyridylmethyl)-4-pyrimidone
(c) 2-[2-(5-methylaminomethyl-2-thienylmethylthio)ethylamino]-5-(3-pyridylmethyl)-4-pyrimidone
(d) 2-[2-(5-(1-pyrrolidino)methyl-2-thienylmethylthio)ethylamino)-5-(3-pyridylmethyl)-4-pyrimidone
(e) 2-[2-(5-methylethylaminomethyl-2-thienylmethylthio)ethylamino]-5-(3-pyridylmethyl)-4-pyrimidone

EXAMPLE 15

Substitution of 4-methoxypyridine-2-carboxaldehyde for 6-methylpyridine-3-carboxaldehyde in the procedure of Example 3(i)(iii) gave ethyl 3-(4-methoxy-2-pyridyl)propionate as an oil which when formylated and reacted with nitroguanidine and sodium ethoxide by the general procedure of Example 6 (vi-vii) gave 2-nitroamino-5-(4-methoxy-2-pyridylmethyl)pyrimidone m.p. 196°-198° (dec.) (from ethanol-acetic acid) and reaction of this with 2-(5-dimethylaminomethyl-2-furylmethylthio)ethylamine by the procedure of Example 6(viii) gives 2-[2-(5-dimethylaminomethyl-2-furylmethylthio)ethylamino]-5-(4-methoxy-2-pyridylmethyl)-4-pyrimidone. Demethylation of the latter compound with boron tribromide gives 2-[2-(5-dimethylaminomethyl-2-furylmethylthio)ethylamino]-5-(4-hydroxy-2-pyridylmethyl)-4-pyrimidone.

EXAMPLE 16

Substitution of the following 3-(heteroaryl)propionates:
(a) ethyl 3-(2-methoxy-3-pyridyl)propionate
(b) ethyl 3-(4,6-dimethoxy-3-pyridyl)propionate
(c) ethyl 3-(2,6-dimethoxy-4-pyridyl)propionate
(d) ethyl 3-(4,5-dimethoxy-2-pyridyl)propionate
(e) ethyl 3-(5-hydroxy-2-pyridyl)propionate
(f) ethyl 3-(4-hydroxy-2-pyrimidyl)propionate
(g) ethyl 3-(4-hydroxy-5-methoxy-2-pyridyl)propionate
(h) ethyl 3-(4-hydroxy-3-methoxy-2-pyridyl)propionate
(i) ethyl 3-(4,5-dimethyl-2-thienyl)propionate
(j) ethyl 3-(6-amino-3-pyridyl)propionate
(k) ethyl 3-(4-isoquinolyl)propionate
(l) ethyl 3-(3-chloro-2-pyridyl)propionate for ethyl 3-(3-pyridyl)propionate in the procedure of Example 3(iv)-(v) and fusion of the resultant 2-methylthio-4-pyrimidones with 2-(5-dimethylaminomethyl-2-furylmethylthio)-ethylamine gives the corresponding 2-[2-(5-dimethylaminomethyl-2-furylmethylthio)ethylamino]-5-heteroarylmethyl)-4-pyrimidones.

The starting materials may be prepared by condensing the corresponding heterocyclic carboxaldehyde with (i) malonic acid, and hydrogenating and esterifying the products or (ii) diethyl malonate, reducing the product with sodium borohydride followed by hydrolysis, monodecarboxylation and esterification, or by reacting a halomethylheterocyclic derivative with sodium and diethyl malonate, and hydrolysing, monodecarboxylating and esterifying the product.

EXAMPLE 17

Substitution of the following 3-arylpropionates:
(a) ethyl 3-(6-(2,3-dihydro-1,4-benzodioxinyl)propionate
(b) ethyl 3-(3-benzyloxyphenyl)propionate
(c) ethyl 3-(3-methoxymethoxyphenyl)propionate (prepared by reacting ethyl 3-(3-hydroxyphyl)propionate with dimethoxyethane)
(d) ethyl 3-(3-trifluoromethylphenyl)propionate
(e) ethyl 3-(4-dimethylaminophenyl)propionate
(f) ethyl 3-(4-phenoxyphenyl)propionate
(g) ethyl 3-(4-(4-chlorophenoxy)phenyl)propionate
(h) ethyl 3-(4-(4-methoxyphenoxy)phenyl)propionate
(i) ethyl 3-(4-biphenylyl)propionate
(j) ethyl 3-(4'-chloro-4-biphenylyl)propionate
(k) ethyl 3-(4'-methoxy-4-biphenylyl)propionate for ethyl 3-(3-pyridyl)propionate in the procedure of Example 3(iv)-(vi) gives the corresponding 2-[2-(5-dimethylaminomethyl-2-furylmethylthio)ethylamino]-5-(arylmethyl)-4-pyrimidones.

Treatment of the product from (c) with hydrochloric acid gives the 5-(3-hydroxybenzyl)pyrimidone.

EXAMPLE 18

Substitution of the following 3-(heteroaryl)propionates:
(a) ethyl 3-(2-furyl)propionate
(b) ethyl 3-(2-thiazolyl)propionate
(c) ethyl 3-(5-oxazolyl)propionate
(d) ethyl 3-(3-isothiazolyl)propionate
(e) ethyl 3-(2-pyrimidyl)propionate
(f) ethyl 3-(5-pyrimidyl)propionate (g) ethyl 3-(2-pyrazyl)propionate
(h) ethyl 3-(4-pyridazyl)propionate
(i) ethyl 3-(2-(5-amino-1,3,4-thiadiazolyl)propionate
(j) ethyl 3-(1-isoquinolyl)propionate
(k) ethyl 3-(4-(1,3-dioxolo[4,5-C]-pyridyl)propionate
(l) ethyl 3-(2-benzimidazolyl)propionate
(m) ethyl 3-(2-benzthiazolyl)propionate for ethyl 3-(6-methyl)propionate in the procedure of Example 3 (iv)-(vi) gives the corresponding 2-[2-(5-dimethylaminomethyl-2-furylmethylthio]-5-(heteroarylmethyl)-4-pyrimidones.

The starting materials can be prepared as described in Example 16.

EXAMPLE 19

Substitution of 3-(2-[1-(4-methoxybenzyl)imidazolyl])acrylic acid for 3-(6-methyl-3-pyridyl)acrylic acid in the procedure of Example 3 and deprotection of the product with anisole and hydrogen bromide in acetic acid gives 2-[2-(5-dimethylaminomethyl-2-furylmethylthio)ethylamino]-5-(2-imidazolylmethyl)-4-pyrimidone.

EXAMPLE 20

(i) Ethyl 3-(6-methyl-3-pyridyl)propionate was formylated with ethyl formate and sodium hydride in 1,2-dimethoxyethane to give ethyl 2-formyl-3-(6-methyl-3-pyridyl)propionate m.p. 142°–144°.

(ii) A solution of ethyl 2-formyl-3-(6-methyl-3-pyridyl)propionate (1.55 g) in methanol (20 ml) was added to a solution of sodium methoxide (from 0.161 g sodium) in methanol (20 ml). Dried nitroguanidine (0.729 g) was added over 5 minutes and the mixture was stirred and boiled under reflux overnight and evaporated to dryness. The residue was dissolved in water (50 ml) and the solution was extracted with chloroform (2×25 ml, discarded) and acidified to pH 5 with acetic acid. The solid which precipitated out was filtered off and recrystallised from methanol-acetic acid to give 2-nitroamino-5-(6-methyl-3-pyridylmethyl)-4-pyrimidone (0.5 g) m.p. 215°–216° (decomp.).

(iii) A solution of 2-nitroamino-5-(6-methyl-3-pyridylmethyl)-4-pyrimidone (0.52 g) and 2-(5-dimethylaminomethyl-2-furylmethylthio)ethylamine (0.43 g) in pyridine (20 ml) was boiled under reflux for 20 hours and evaporated to dryness. The residual oil was dissolved in hot propanol and the solution was acidified with ethanolic hydrogen chloride.

The solid which crystallised on cooling was filtered off to give 2-[2-(5-dimethylaminomethyl-2-furylmethylthio)ethylamino]-5-(6-methyl-3-pyridylmethyl)-4-pyrimidone trihydrochloride (0.84 g) m.p. 232°–237°. A sample recrystallised from ethanol containing hydrogen chloride had m.p. 236°–240°.

EXAMPLE 21

Cystamine is reacted with 2-nitroamino-5-(6-methyl-3-pyridylmethyl)-4-pyrimidone by heating in ethanol to give 2-[5-(3-pyridylmethyl)-4-oxo-2-pyrimidylamino]ethyl disulphide which is reduced with dithiothreitol to give 2-(2-mercaptoethylamino)-5-(6-methyl-3-pyridylmethyl)-4-pyrimidone which is reacted with 5-dimethylaminomethyl-2-furylmethanol in cold aqueous hydrochloric acid to give 2-[2-(5-dimethylaminomethyl-2-furylmethylthio)ethylamino]-5-(6-methyl-3-pyridylmethyl)-4-pyrimidone.

EXAMPLE 22

2-(5-Hydroxymethyl-2-furylmethyl)-1H-isoindole-1,3-(2H)-dione is reacted with cysteamine in cold hydrochloric acid to give 2-(5-(2-aminoethylthiomethyl-2-furylmethyl)-1H-isoindole-1,3-(2H)dione which is reacted with 2-nitroamino-5-(6-methyl-3-pyridylmethyl)-4-pyrimidone by heating in ethanol and the product is deprotected with hydrazine to give 2-[2-(5-aminomethyl-2-furylmethylthio)ethylamino]-5-(6-methyl-3-pyridylmethyl)-4-pyrimidone. Treatment of this amine with formaldehyde and formic acid gives the product of Example 3.

EXAMPLE 23

(i) Ethoxycarbonylmethyltriphenylphosphonium bromide (100 g) in ethanol (500 ml) was added with stirring under nitrogen to a solution of sodium ethoxide (from 4.28 g sodium) in ethanol (100 ml). 3-Acetylpyridine (18.8 g) in ethanol (300 ml) was added dropwise over 0.5 hour. The mixture was allowed to stand for 14 days and was evaporated to dryness. The residue was taken up in water, the pH adjusted to 8.5 and the mixture was extracted with benzene. The extract was dried, evaporated and the residue was distilled at reduced pressure to give ethyl 3-(3-pyridyl)-crotonate (13.39 g) b.p. 78°/0.1 mmHg.

(ii) Ethyl 3-(3-pyridyl)crotonate (13.2 g) was hydrogenated in ethanol (130 ml) at 270 kPa with 10% palladium on charcoal catalyst for 3 hours at room temperature to give ethyl 3-(3-pyridyl)butyrate (12.74 g), b.p. 74°–80°/0.15 mmHg.

(iii) A mixture of ethyl 3-(3-pyridyl)butyrate (13.8 g) and ethyl formate (7.94 g) was added dropwise over 3 hours to a stirred suspension of sodium hydride (2.14 g) in dry glyme (35 ml) under nitrogen at 0°. The mixture was stirred at room temperature for 18 hours. The solution was poured onto ice/water and the mixture was extracted at pH 13 with ether. The aqueous solution was adjusted to pH 7.0 and allowed to stand at 0° overnight. The solid was filtered off to give ethyl 2-formyl 3-(3-pyridyl)butyrate (5.68 g) as a pale brown solid m.p. 128°–31° (from 2-propanol).

(iv) Thiourea (1.4 g) and ethyl 2-formyl-3-(3-pyridyl)-butyrate (3.4 g) was added to a solution of sodium ethoxide (from 0.78 g sodium) in ethanol (45 ml). The mixture was heated under reflux for 7 hours and evaporated. The residue was taken up in water and extracted with chloroform at pH 13. The pH was adjusted to 7.0 and the mixture allowed to stand at 0° overnight. The solid was filtered off to give 5-[1-(3-pyridyl)ethyl]-2-thiouracil (1.83 g) m.p. 225°–228° (from 2-propanol).

(v) 5-[1-(3-Pyridyl)ethyl]-2-thiouracil (3.4 g) was added to a solution of sodium ethoxide (from 0.74 g sodium) in ethanol (35 ml). Methyl iodide (2.42 g) was added over 0.5 hour at 0°. After standing for a further 2 hours at 0° the solution was evaporated to dryness. The residue was taken up in water and the pH adjusted to 7.0 and the mixture was allowed to stand at 0° overnight. The solid was filtered off to give 2-methylthio-5-[1-(3-pyridyl)ethyl]-4-pyrimidone (3.04 g) m.p. 201°–204° (from ethanol).

(vi) Equimolar amounts of 2-methylthio-5-[1-(3-pyridyl)ethyl]-4-pyrimidone and 2-(5-dimethylaminomethyl-2-furylmethylthio)ethylamine in pyridine are boiled under reflux for 48 hours and evaporated to dryness. The residue is purified to give 2-[2-(5-dimethylaminomethyl-2-furylmethylthio)ethylamino]-5-(1-(3-pyridyl)ethyl)-4-pyrimidone.

EXAMPLE 24

(i) A mixture of 2-methoxy-5-cyanopyridine (61.26 g), semicarbazide hydrochloride (76.4 g), sodium acetate (74.92 g), ethanol (1300 ml) and water (400 ml) was hydrogenated at 344 kPa using Raney nickel catalyst (1.0 g). The mixture was evaporated to a volume of 500 ml, water (1000 ml) was added and the mixture was allowed to stand at 0° overnight. The mixture was filtered and the solid was washed with water and dissolved in 10% hydrochloric acid (1000 ml). Formaldehyde solution (36% w/v, 450 ml) was added and the mixture was warmed for 15 minutes, allowed to cool and was added to a solution of sodium acetate (298.5 g) in water (900 ml). This mixture was extracted with ether (3×500 ml) and the combined extracts were successively washed with aqueous potassium carbonate and water and were dried and evaporated to give 6-methoxypyridine-3-carboxaldehyde (31.5 g, 50%) m.p. 48°–49°.

(ii) A mixture of 6-methoxypyridine-3-carboxaldehyde (2.34 g), monoethyl malonate (4.51 g), pyridine (12 ml) and piperidine (6 drops) was heated under reflux for 5 hours and was evaporated to an oil. This oil was partitioned between ether and dilute aqueous ammonia. The ether layer was washed with water and evaporated to an oil which crystallised on standing to give ethyl 3-(6-methoxy-3-pyridyl)acrylate (2.8 g, 79%) m.p. 49°–52°.

(iii) Ethyl 3-(6-methoxy-3-pyridyl)acrylate (32.33 g) in ethanol (160 ml) was hydrogenated at 344 kPa at 40°. using palladium-on-charcoal catalyst (5%, 0.2 g). The mixture was filtered and the filtrate was evaporated to give ethyl 3-(6-methoxy-3-pyridyl)propionate (32.7 g) as an oil.

(iv) A mixture of ethyl 3-(6-methoxy-3-pyridyl)propionate (32.74 g) and ethyl formate (17.22 g) was added dropwise over 1.5 hours to a stirred suspension of sodium hydride in oil (50%, 9.38 g) in 1,2-dimethoxyethane (50 ml) cooled to −2°, allowed to stand overnight at room temperature and was poured on to ice. The mixture was extracted with ether (discarded), and the aqueous phase was adjusted to pH 5 with 2N sulphuric acid. An oil was precipitated and crystallised on standing to give ethyl 2-formyl-3-(6-methoxy-3-pyridyl)propionate (25.9 g, 70%) m.p. 91.5°–94°. A sample recrystallised from aqueous ethanol had m.p. 93°–94°.

(v) Nitroguanidine (4.7 g) was added to a solution of sodium methoxide (prepared from 1.15 g sodium) in methanol (50 ml) and the mixture was refluxed for 45 minutes. Ethyl 2-formyl-3-(6-methoxy-3-pyridyl)propionate (10.7 g) was added and the mixture was refluxed for 34 hours and evaporated to a residue. This residue was dissolved in water and the solution was extracted with chloroform (subsequently discarded). The aqueous solution was adjusted to pH 5 with acetic acid, and the solid which precipitated out was filtered off to give 2-nitroamino-5-(6-methoxy-3-pyridylmethyl)-4-pyrimidone m.p. 183.5°–186°.

(vi) An equimolar mixture of 2-nitroamino-5-(6-methoxy-3-pyridylmethyl)-4-pyrimidone and 2-(5-dimethylaminomethyl-2-furylmethylthio)ethylamine are refluxed in ethanol for 18 hours and evaporated to dryness. The residue is triturated with water and recrystallised to give 2-[2-(5-dimethylaminomethyl-2-furylmethylthio)ethylamino]-5-(6-methoxy-3-pyridylmethyl)-4-pyrimidone.

(vii) The product of part (vi) is refluxed in 2N hydrogen chloride in ethanol for 24 hours to give 2-[2-(5-dimethylaminomethyl-2-furylmethylthio)ethylamino]-5-(6-hydroxy-3-pyridylmethyl)-4-pyrimidonetrihydrochloride.

EXAMPLE 25

Reaction of 2-methylthio-5-methyl-4-pyrimidone with one equivalent of 2-(5-dimethylaminomethyl-2-furylmethylthio)ethylamine by boiling under reflux in pyridine for 48 hours gives 2-[2-(5-dimethylaminomethyl-2-furylmethylthio)ethylamino]-5-methyl-4-pyrimidone.

EXAMPLE 26

Substitution of
(a) ethyl octanoate
(b) ethyl 3-cyclohexylpropionate for ethyl 3-(6-methyl-3-pyridyl)propionate in the procedure of Example 3(iv)–(vi) gives
(iv)(a) 5-hexyl-2-thiouracil m.p. 169.5°–172° (from aqueous ethanol)
(b) 5-cyclohexylmethyl-2-thiouracil m.p. 210°–211° (from ethanol)
(v)(a) 5-hexyl-2-methylthio-4-pyrimidone m.p. 116°–117.5° (from aqueous ethanol)
(b) 5-cyclohexylmethyl-2-methylthio-4-pyrimidone m.p. 187°–188° (from acetic acid)
(vi)(a) 2-[2-(5-dimethylaminomethyl-2-furylmethylthio)ethylamino]-5-hexyl-4-pyrimidone
(b) 2-[2-(5-dimethylaminomethyl-2-furylmethylthio)ethylamino]-5-cyclohexylmethyl-4-pyrimidone

EXAMPLE 27

A pharmaceutical composition is prepared from the following ingredients:
2-[2-(5-dimethylaminomethyl-2-furylmethylthio)ethylamino]-5-(6-methyl-3-pyridylmethyl)-4-pyrimidone trihydrochloride: 150 mg,
Sucrose: 75 mg,
Starch: 25 mg,
Talc: 5 mg,
Stearic Acid: 2 mg.

The ingredients are screened, mixed and filled into a hard gelatin capsule.

The other compounds of Structure 1 can be formulated into pharmaceutical compositions in a similar manner, and these compositions are administered to a subject within the dose ranges given above to block histamine $H_2$-receptors.

What is claimed is:
1. A compound of the formula:

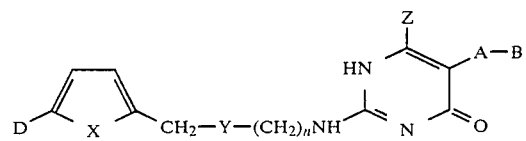

in which D is hydrogen or $R^1R^2N(CH_2)_m-$, $R^1$ and $R^2$ are hydrogen, lower alkyl, phenyl(lower alkyl) or $R^1$ and $R^2$ taken together with the nitrogen atom shown can form a pyrrolidino or piperidino group, m is from 1 to 6, X is oxygen or sulphur, Y is sulphur, oxygen or methylene, n is 2 or 3, Z is hydrogen or lower alkyl, A is $C_1$-$C_5$ alkylene or $-(CH_2)_pW(CH_2)_q-$ where W is oxygen or sulphur and p and q are such that their sum is from 1 to 4, and B is hydrogen, methyl, $C_3$-$C_6$ cycloalkyl, a heteroaryl group selected from furyl, thienyl, thiazolyl, oxazolyl, isothiazolyl, imidazolyl, thiadiazolyl, benzimidazolyl and benzthiazolyl, said heteroaryl group being optionally substituted by one or more of the groups lower alkyl, lower alkoxy, halo, hydroxy and amino, or B is a naphthyl, or a 4- or 5-(1,3-benzodioxolyl) group, or a phenyl group optionally substituted with one or more lower alkyl, lower alkoxy, halogen, phenyl(lower alkoxy), hydroxy, lower alkoxylower alkoxy, trifluoromethyl, di(lower alkyl)amino, phenoxy, halophenoxy, lower alkoxyphenoxy, phenyl, halophenyl or lower alkoxyphenyl groups, in the form of the free base or its pharmaceutically acceptable acid addition salts.

2. A compound of claim 1 in which $R^1$ and $R^2$ are hydrogen, lower alkyl or 2-phenylethyl or $R^1$ and $R^2$ taken together with the nitrogen atom shown can form a pyrrolidino or piperidino group.

3. A compound of claim 2 in which $R^1$ and $R^2$ are both methyl.

4. A compound of claims 1, 2 or 3 in which m is 1 to 3.

5. A compound of claim 1 in which D is hydrogen.

6. A compound of claim 1 in which X is oxygen.

7. A compound of claim 1 in which Y is sulphur or methylene.

8. A compound of claim 1 in which Y is sulphur.

9. A compound of claim 1 in which n is 2.

10. A compound of claim 1 in which Z is methyl.

11. A compound of claim 1 in which Z is hydrogen.

12. A compound of claim 1 in which A is α,ω-straight alkylene.

13. A compound of claim 12 in which A is methylene.

14. A compound of claim 1 in which A is —($CH_2$)$_p$W($CH_2$)$_q$— where p is 0, W is oxygen and q is 1.

15. A compound of claim 1 in which B is a 2-furyl, 2-thienyl, 2-thiazolyl or 2-imidazolyl group, which group is optionally substituted by one or more lower alkyl or lower alkoxy groups.

16. A compound of claim 1 in which B is a 5-(1,3-benzodioxolyl) or 1-naphthyl group.

17. A compound of claim 1 in which B is a phenyl group substituted by one or more lower alkoxy groups.

18. A compound of claim 17 in which B is 3-methoxyphenyl, 4-methoxyphenyl or 3,4-dimethoxyphenyl.

19. The compound of claim 16, said compound being 2-[2-(5-dimethylaminomethyl-2-furylmethylthio)ethylamino]-5-[5-(1,3-benzodioxolyl)methyl]-4-pyrimidone.

20. A pharmaceutical composition having histamine $H_2$-receptor blocking activity comprising in an effective amount to block said receptors a compound of claim 1 and a pharmaceutically acceptable diluent or carrier.

21. A method of blocking histamine $H_2$-receptors which comprises administering to an animal in need thereof in an effective amount to block said receptors a compound of claim 1.

22. A method of simultaneously blocking histamine $H_1$-receptors and histamine $H_2$-receptors which comprises administering to an animal in need thereof in an effective amount to block said receptors a compound of claim 5.

23. A compound of claim 1 in which B is a heteroaryl group selected from furyl, thienyl, thiazolyl, oxazolyl, isothiazolyl, imidazolyl, thiadiazolyl, benzimidazolyl or benzthiazolyl, which group is optionally substituted by one or more lower alkyl, lower alkoxy, halo, hydroxy or amino groups.

24. The compound 2-[2-(5-dimethylaminomethyl-2-furylmethylthio)ethylamino]-5-(4-chlorophenylmethyl)-4-pyrimidone.

25. A compound of the formula:

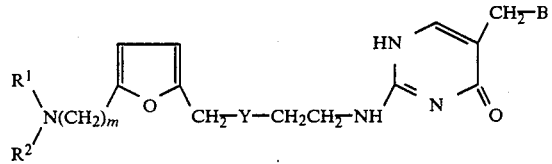

in which:
$R^1R^2N$ is a methylamino or dimethylamino group;
m is from 1 to 4;
Y is sulphur or methylene; and
B is 5-(1,3-benzodioxolyl) or phenyl substituted by lower alkoxy or halogen.

* * * * *

UNITED STATES PATENT AND TRADEMARK OFFICE
CERTIFICATE OF CORRECTION

PATENT NO. : 4,539,207

DATED : September 3, 1985

INVENTOR(S) : Thomas H. Brown and Robert J. Ife

It is certified that error appears in the above-identified patent and that said Letters Patent is hereby corrected as shown below:

On the first page of the patent, in the left-hand column, following item [62] insert the following:

[30]  Foreign Application Priority Data

February 13, 1978    United Kingdom 5740/78
    May 25, 1978    United Kingdom 22834/78
    November 13, 1978    United Kingdom 44259/78

Signed and Sealed this

Seventh Day of January 1986

[SEAL]

Attest:

DONALD J. QUIGG

Attesting Officer

Commissioner of Patents and Trademarks